US012611255B2

(12) United States Patent
Cardinale et al.

(10) Patent No.:    US 12,611,255 B2
(45) Date of Patent:         Apr. 28, 2026

(54) SURGICAL SYSTEMS, METHODS, AND DEVICES EMPLOYING AUGMENTED REALITY (AR) FOR PLANNING

(71) Applicant: Depuy Synthes Products, Inc., Raynham, MA (US)

(72) Inventors: Michael D. Cardinale, Hillsborough, NJ (US); Cory Emil, Milton, MA (US); Roman Lomeli, Plymouth, MA (US); Joseph A. Algeri, West Bridgewater, MA (US); Sandi Glauser, Parkland, FL (US); James R. Brownhill, Norton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 365 days.

(21) Appl. No.: 18/122,793

(22) Filed: Mar. 17, 2023

(65) Prior Publication Data

US 2023/0293238 A1      Sep. 21, 2023

Related U.S. Application Data

(60) Provisional application No. 63/321,618, filed on Mar. 18, 2022.

(51) Int. Cl.
*A61B 34/10*          (2016.01)
*A61B 34/20*          (2016.01)
*A61B 90/00*          (2016.01)

(52) U.S. Cl.
CPC .............. *A61B 34/10* (2016.02); *A61B 34/20* (2016.02); *A61B 90/361* (2016.02);
(Continued)

(58) Field of Classification Search
CPC ....... A61B 34/10; A61B 34/20; A61B 90/361; A61B 2034/107; A61B 2034/2055;
(Continued)

(56) References Cited

U.S. PATENT DOCUMENTS

2013/0293578 A1* 11/2013 Leung ................... A61B 34/20
                                                                    345/633
2016/0287337 A1   10/2016 Aram et al.
(Continued)

FOREIGN PATENT DOCUMENTS

WO          2010/102197 A2      9/2010
WO          2021/007418 A2      1/2021
(Continued)

OTHER PUBLICATIONS

Rong Wen, Wei-Liang Tay, Binh P. Nguyen, Chin-Boon Chng, Chee-Kong Chui, Hand gesture guided robot-assisted surgery based on a direct augmented reality interface, Computer Methods and Programs in Biomedicine, vol. 116, Issue 2 (Year: 2014).*
(Continued)

*Primary Examiner* — Said Broome
(74) *Attorney, Agent, or Firm* — Condo Roccia Koptiw LLP

(57)                    ABSTRACT

Described are methods and systems for computer aided surgery (CAS) comprising an augmented reality (AR) system configured to display augmented reality information including a virtual control element, a position tracking system separate from the AR system, wherein the position tracking system is configured to track positions of a physical object for interacting with the virtual control element, a controller configured to: receive planning information for a surgical procedure; determine a first input indicating that the physical object is interacting with the virtual control element; determine a change in position of the physical object
(Continued)

interacting with the virtual control element indicating a first adjustment to a parameter of the planning information; receive a second input that either indicates a second adjustment to a parameter of the planning information different from the first adjustment or confirms the first adjustment to the planning information; and store the adjustment to the planning information.

20 Claims, 6 Drawing Sheets

(52) U.S. Cl.
CPC . *A61B 2034/107* (2016.02); *A61B 2034/2055* (2016.02); *A61B 2034/2065* (2016.02); *A61B 2090/365* (2016.02)

(58) Field of Classification Search
CPC ...... A61B 2034/2065; A61B 2090/365; A61B 2090/502; A61B 2090/372; A61B 2090/3983; A61B 90/36; G06F 1/163; G06F 3/014; G06F 3/011; G06F 3/017; G06F 3/0325; G06F 3/0482; G06F 3/04842

See application file for complete search history.

(56) References Cited

U.S. PATENT DOCUMENTS

| | | |
|---|---|---|
| 2018/0325610 A1 | 11/2018 | Cameron et al. |
| 2019/0053855 A1 | 2/2019 | Siemionow et al. |
| 2021/0106386 A1 | 4/2021 | Lang |
| 2021/0275253 A1* | 9/2021 | Moctezuma De La Barrera ........ G06F 3/0484 |
| 2021/0378752 A1 | 12/2021 | Paul et al. |
| 2021/0382559 A1* | 12/2021 | Segev ..................... G06F 3/013 |

FOREIGN PATENT DOCUMENTS

| | | |
|---|---|---|
| WO | 2021/011760 A1 | 1/2021 |
| WO | 2021/163039 A1 | 8/2021 |

OTHER PUBLICATIONS

Daniel Ashbrook et. la.2016. Bitey:an exploration of tooth click gestures for hands-free user interface control. In Proceedings of the 18th International Conference on Human-Computer Interaction with Moile Devices and Services (MobileHCI '16).Association for Computing Machinery, New York, NY,USA, 158-169 (Year: 2016).*

Scherl C, Stratemeier J, Rotter N, Hesser J, Schönberg SO, Servais JJ, Männle D, Lammert A. Augmented Reality with HoloLens® in Parotid Tumor Surgery: A Prospective Feasibility Study. ORL J Otorhinolaryngol Relat Spec. 2021;83(6):439-448. (Year: 2021).*

Qian et al., "ARssist: Augmented Reality on a Head-Mounted Display for the First Assistant in Robotic Surgery", Healthcare Technology Letters, vol. 5, No. 5, 2018, pp. 194-200.

Medtronic Navigation, Inc., "StealthStation S7 Treatment Guidance System Manual", A Guide to Understanding the StealthStation S7 Treatment Guidance System, Part No. 9733782, revision 14, 2007-2012, 74 pages.

Smith & Nephew, "RI. Hip Navigation Total Hip Arthroplasty, Surgical Technique—Lateral Position", 28 pages.

Brainlab, "Knee 3 Surgical Technique", Brainlab, 2015, 58 pages.

Patil, "A modified stereotactic frame as an instrument holder for frameless stereotaxis: Technical note", Surgical Neurology International, http://www.surgicalneurologyint.com/text.asp? 2010/1/1/62/70957, Oct. 2010, 5 pages.

Spine Navigation Clinical Workflow, https:/www.brainlab.com/video-player/gRIL88A/, Jan. 19, 2021.

* cited by examiner

Controller

Navigation / Tracking

Accessories

AR Device

Interface

Intra-op Planning

Library and Customizable Display Controls

Navigating Instruments (to trajectory, to plane, etc)

AR Device (HMD, Headset, etc.)

Real world scene (patient)

Overlaid information

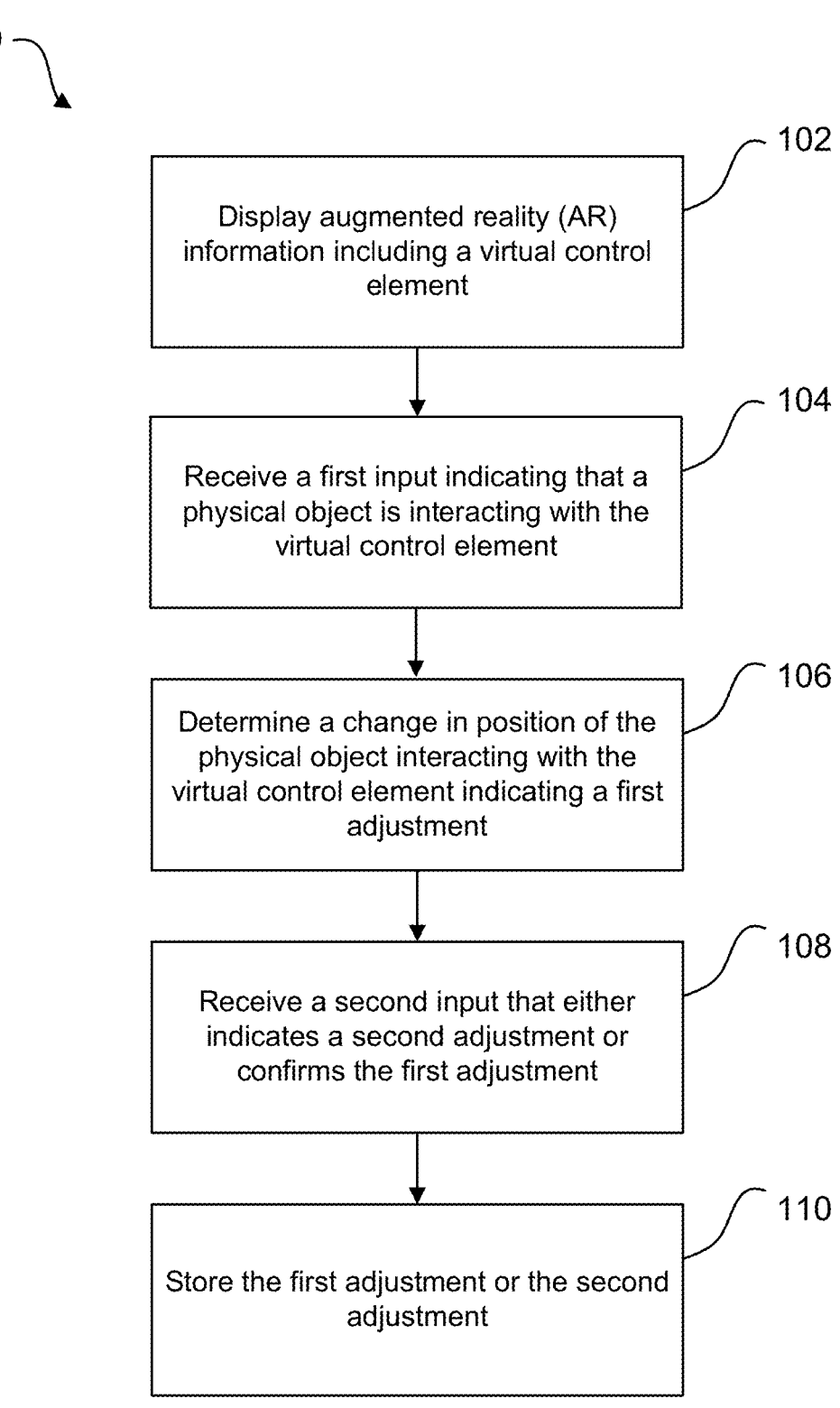

100

102
Display augmented reality (AR) information including a virtual control element 104
Receive a first input indicating that a physical object is interacting with the virtual control element 106
Determine a change in position of the physical object interacting with the virtual control element indicating a first adjustment 108
Receive a second input that either indicates a second adjustment or confirms the first adjustment 110
Store the first adjustment or the second adjustment

FIG. 4

User
Interface
Block

Single Use Card

Alignment
Tab

User
Interface
Block

SURGICAL SYSTEMS, METHODS, AND DEVICES EMPLOYING AUGMENTED REALITY (AR) FOR PLANNING

CROSS REFERENCE TO RELATED APPLICATION

This application claims priority to U.S. Provisional Application Ser. No. 63/321,618, filed Mar. 18, 2022, the contents of which are hereby incorporated by reference in its entirety.

BACKGROUND

Many surgical procedures require large amounts of information for planning and/or undertaking the procedure. One way to manage this is to improve the way information is presented to a user, e.g., a surgeon.

Augmented Reality (AR) provides an overlay of virtual information on or adjacent to a "real-world" object visually perceived by a user, usually through an AR device such as a headset, Google Glass, etc. An AR device is configured to display information, such as pictures, video, text, warnings, models, simulations, etc., while not obscuring the user's view of the real-world objects in their proximity.

However, the information displayed may be selectable, pertinent, and customizable. For example, intra-op planning and navigation can greatly benefit from AR systems, provided it does not negatively impact workflow. Moreover, implementations for navigation among various information types is challenging in a surgical setting, and requires innovative solutions. Furthermore, specific use cases may present challenges that can at least be ameliorated by properly configured AR systems.

Accordingly, there is a need for improved systems, methods, and devices to employ AR that can improve patient outcomes and surgical efficiency.

BRIEF DESCRIPTION OF THE DRAWINGS

FIG. 4 is a flowchart of a process of the CAS system.

SUMMARY

Described are methods and systems for computer aided surgery (CAS) comprising an augmented reality (AR) system configured to display augmented reality information including a virtual control element, a position tracking system separate from the AR system, wherein the position tracking system is configured to track positions of a physical object for interacting with the virtual control element, a controller configured to: receive planning information for a surgical procedure; determine a first input indicating that the physical object is interacting with the virtual control element; determine a change in position of the physical object interacting with the virtual control element indicating a first adjustment to a parameter of the planning information; receive a second input that either indicates a second adjustment to a parameter of the planning information different from the first adjustment or confirms the first adjustment to the planning information; and store the adjustment to the planning information.

DETAILED DESCRIPTION

Figure 1:
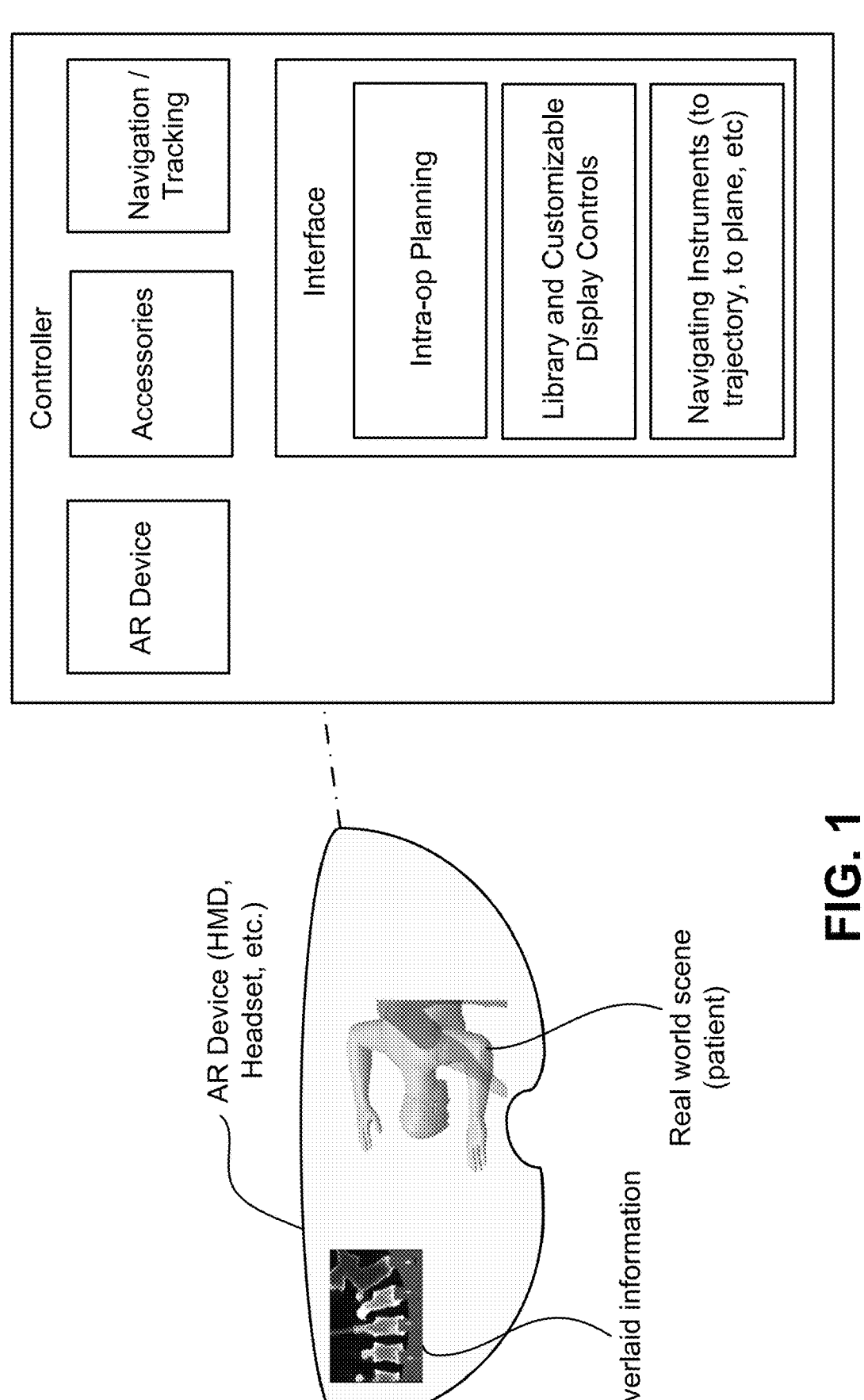
FIG. 1 depicts a computer aided surgery (CAS) system employing Augmented Reality (AR).

FIG. 1 depicts a system for Augmented Reality (AR) in a surgical setting. A user (e.g., surgeon) views a patient or other real-world object (instruments, operating room (OR) features, etc.) while receiving an overlay of virtual information from the controller. The information may be stored information or streamed information. Examples of information include pictures, video, text, warnings, models, simulations, etc. The information displayed may be selectable, pertinent, and customizable. For example, intra-op planning, navigation and robotics may greatly benefit from AR systems, provided it does not negatively impact workflow. Moreover, implementations for managing various information types (such as within a library) is challenging in a surgical setting. Furthermore, specific use cases, such as position-finding of instruments relative to a patient, may present challenges that may be at least ameliorated by properly configured AR systems.

Methods and implementations are provided to assist a surgeon to perform intra-operative (intra-op) visualization and/or planning from an AR headset, with minimal impact to their workflow. AR provides control to the surgeon, for example, for orthopedic procedures. Example applications include knee surgery (e.g., total knee arthroplasty (TKA), uni-compartmental knee arthroplasty (UKA), or knee ligament reconstruction), hip surgery (e.g., hip arthroplasty or femoral acetabular impingement), shoulder surgery (e.g., shoulder arthroplasty, glenoid bone augmentation or cuff repair), spine surgery (e.g., spinal fusion), and other orthopedic surgeries. In some embodiments, the system may enhance what the surgeon may see and help the surgeon visualize what they can't see. The display may include a 3D CT model overlayed on native anatomy or suspended above the patient. The display may include virtual targets on the anatomy and information related to the instrument relative to the target. The display may include simultaneous high resolution video feeds (blood flow, nerves, etc.). There may be a contextual content to a current step in the workflow (e.g., a bone overlay may not be needed at the same time as seeing nerve or blood flow).

Provided is an AR system that has a user interface (e.g., with a controller) and a display, such as is typically associated with a headset. As will be described, navigation/tracking may be provided. In some embodiments, this application is directed to computer aided surgery (CAS) comprising an augmented reality (AR) system configured to display augmented reality information, a position tracking system configured to track positions of objects, an instrument coupled to a navigational tracker detectable by the position tracking system, and a controller configured to determine a position of the instrument, based on the determined position, display augmented reality information using the AR system. The controller may be used to send and receive information to and from the AR system or to other digitally connected systems (e.g., robot). The controller typically includes a power supply, AC/DC converters, control system interface circuits, and other components included in computer aided surgery. The controller is also configured to perform the systems and methods described herein. Particularly precise location (e.g., position and orientation) information may allow a user better control, e.g., for planning or navigating a virtual menu, while minimizing a need to look away from a patient.

Figure 2:
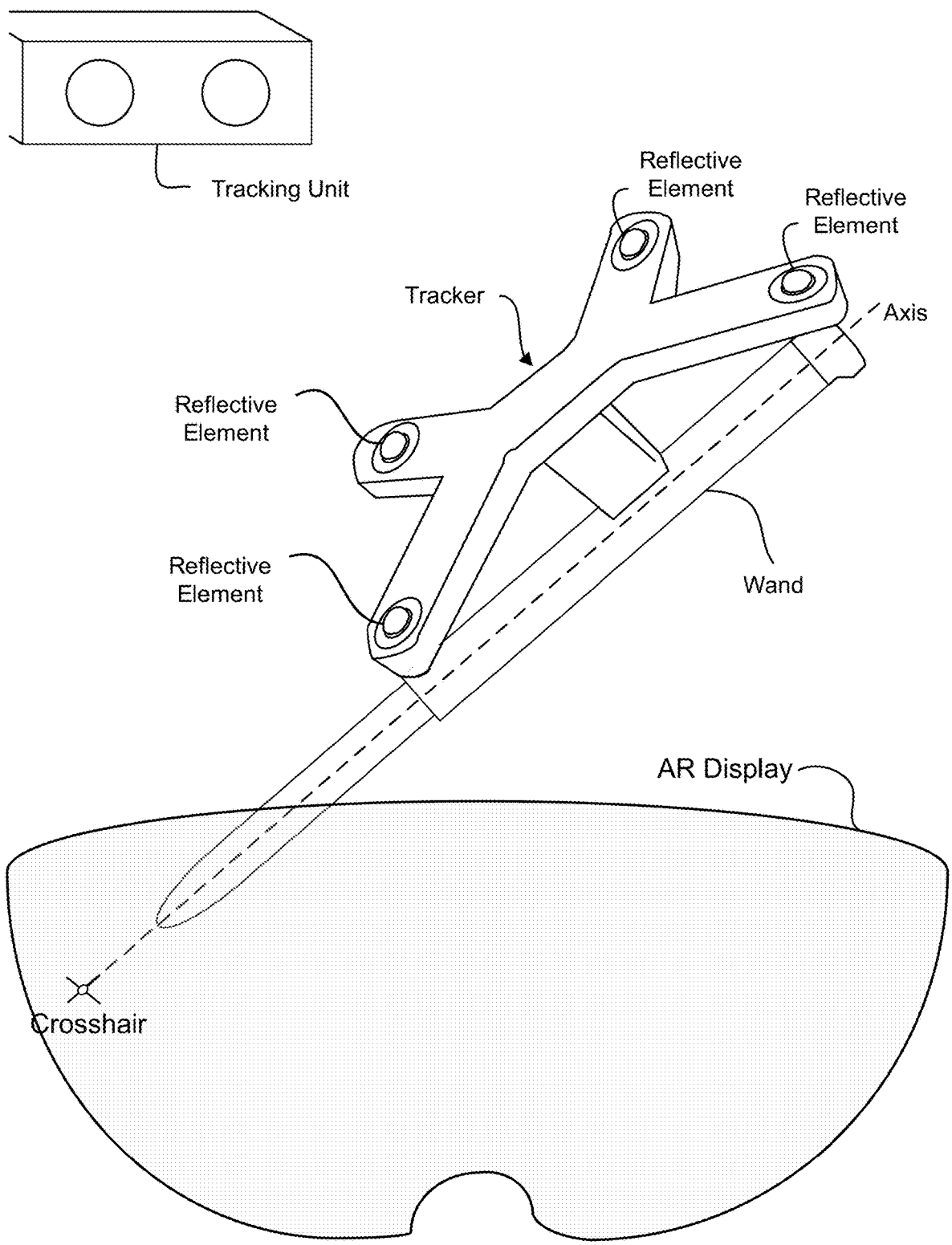
FIG. 2 depicts a schematic of a wand with a navigational tracker.

FIG. 2 depicts a schematic of a wand with a navigational tracker. The CAS system may include a position tracking system. The position tracking system may comprise a tracking unit in communication with the controller. The tracking unit may include one or more navigation system cameras that may capture a position of the markers (e.g., reflective elements as depicted). The navigation cameras may be stereoscopic. The relative pose or three-dimensional position (e.g., location and orientation) of a tracker may be tracked and shared with the controller. The tracking unit may measure the relative motions between any and all trackers in real time. In an alternative embodiment, the navigation cameras may be attached to a surface of an AR headset provided that they are supplementary cameras to the originally manufactured equipment.

The position tracking system may include a tracker having a plurality of navigational features allowing the controller (via the tracking unit) to determine a position (e.g., location and orientation in a three-dimensional space) of the tracker. As depicted, the tracker comprises a navigation array including a plurality of markers in a unique constellation or geometric arrangement. For example, optical navigation or tracking systems may utilize stereoscopic sensors (of the tracking unit) to detect light emitting diodes (LEDs) or infra-red (IR) light reflected or emitted from one or more optical markers affixed to the array. For example, when the markers are reflective elements, as illustrated, once detected by stereoscopic sensors (e.g., navigation cameras), the relative arrangement of the elements in the sensors' field of view, in combination with the known geometric arrangement of the elements, may allow the system to determine a three-dimensional position of the array. Other examples of tracking systems in include ultrasonic sensors, radio-frequency identification (RFID) sensors or other radio frequency (RF) tracking systems, electromagnetic interference (EMI) tracking systems, visual systems including for example chest trackers, Aruco markers, machine vision using shape recognition, etc. Preferably, the position tracking system (e.g., a tracker of the position tracking system) comprises a plurality of reflective elements.

An additional tracker (not depicted) may be attached to a patient or elsewhere in an operating theater (e.g., such as coupled to a surgical table), thus allowing the position of the wand to be relative, such as to define a coordinate system. Alternatively, the CAS system may include shape recognition software to determine surroundings.

The tracker may be attached to a wand. The wand may also be replaced by an instrument relevant to the surgical procedure. The tracker may reveal a position of the wand (or instrument) in three-dimensional space given the known and precise relationship between the tracker and the instrument (rotation, travel, etc.). For example, the controller may be configured to identify a 3D position of a portion of the instrument, such as a tip. Stated differently, the tracker may help provide complete positioning information (e.g., of the wand), which may be used by the controller. In an example, the wand may define an axis. The controller may be configured to determine a projected position extending along the axis of the wand and determine to display a crosshair on the AR system at the projected position. For example, the projected position may be on a surface. It is understood that the crosshair could be replaced with a dot, an arrow, or some other indicator displayed by the AR system.

In an example, the CAS system may comprise a user interface (for example, as may be displayed on the AR display) as will be described. Information displayed on the AR display may mirror a display on a surgical touch screen, such as for planning. Information displayed on the AR display may be a virtual user interface (visible only to the wearer of the AR display). The virtual user interface may have specific parameters that may be adjusted for surgical planning (trajectory, version, inclination, resection depth, or other similar parameters for various orthopedic surgeries, etc.). A surgeon using the tracked wand may interact with the virtual user interface. For example, the position tracking system may interact with the controller to determine where the surgeon is aiming. In some embodiments, the virtual user interface may have one or more virtual buttons. The surgeon may advance the crosshair to a virtual button to make a selection. Selection of a button may require an input. Examples of inputs include one or more of a physical button on the wand configured to send a signal either wired or wirelessly to the controller, a point and hold determination, a finger gesture, a hand gesture, a head gesture, eye gaze, voice, a directional exhale, a foot pedal, or an audible click at a predetermined frequency or frequencies. For example, the audible click may be a result of depressing a metal clicker to create an audible click at a predetermined frequency or frequencies (the controller may be configured to listen for the click, so in some embodiments, audible refers to audible to the controller (advantageously, the click may be audible to the user so that they know the input was made (user feedback)). Stated differently, the audible click may be an acoustic waveform of a predetermined frequency/frequencies and/or amplitude(s). It is understood that combinations of inputs are contemplated as comprising an input, for example, an input may be an eye gaze coupled with a foot pedal press (e.g., within a predetermined time of the eye gaze).

The system may recognize finger gestures (e.g., pointing, crooking, multiple finger gestures (like an "OK," etc.)). Complex hand gestures are contemplated, like open hand to move a position (e.g., target entry point), closed fist to fix position, and then moving forearm relative to fist to adjust trajectory while holding the wand. Different periods of the surgery may use different techniques, for example, certain hand gestures may be used for intra-op planning, as a surgeon's hands should be free, but gaze may be employed during actual cutting or drilling portions of the surgical workflow.

Figure 3:
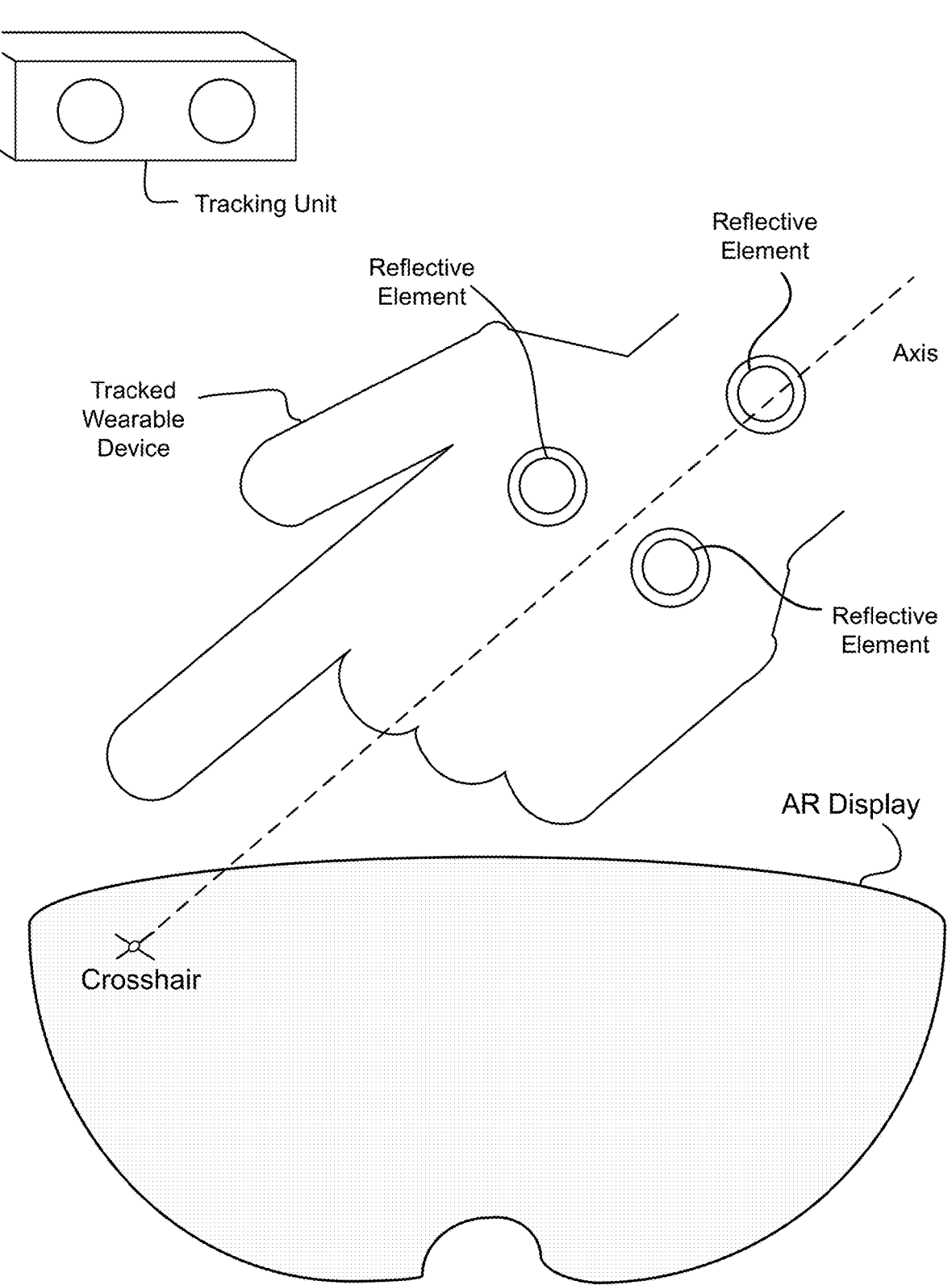
FIG. 3 depicts a schematic of a wearable device with a navigational tracker.

FIG. 3 depicts a schematic of a wearable device with a navigational tracker (e.g., depicted as a glove with a navigational tracker). The CAS system may include a position tracking system. The position tracking system may comprise a tracking unit in communication with the controller. The tracking unit may include one or more navigation system cameras that may capture a position of the markers (e.g., reflective elements as depicted). The navigation cameras may be stereoscopic. The relative pose or three-dimensional position (e.g., location and orientation) of a tracker may be tracked and shared with the controller. The tracking unit may measure the relative motions between any and all trackers in real time.

The position tracking system may include a tracker having a plurality of navigational features allowing the controller (via the tracking unit) to determine a position (e.g., location and orientation in a three-dimensional space) of the tracker. As depicted, the tracker comprises a navigation array including a plurality of markers in a unique constellation or geometric arrangement. For example, optical navigation or tracking systems may utilize stereoscopic sensors (of the tracking unit) to detect light emitting diodes (LEDs) or infra-red (IR) light reflected or emitted from one or more optical markers affixed to the array. For example, when the markers are reflective elements, as illustrated, once detected by stereoscopic sensors (e.g., navigation cameras), the relative arrangement of the elements in the sensors' field of view, in combination with the known geometric arrangement of the elements, may allow the system to determine a three-dimensional position of the array. Other examples of tracking systems in include ultrasonic sensors, radio-frequency identification (RFID) sensors or other radio frequency (RF) tracking systems, electromagnetic interference (EMI) tracking systems, visual systems including for example Aruco markers, etc. Preferably, the position tracking system (e.g., a tracker of the position tracking system) comprises a plurality of reflective elements. In an alternative embodiment, the navigation cameras may be attached to a surface of an AR headset provided that they are supplementary cameras to the originally manufactured equipment.

An additional tracker (not depicted) may be attached to a patient or elsewhere in an operating theater (e.g., such as coupled to a surgical table), thus allowing the position of the wearable device to be relative, such as to define a coordinate system. Alternatively, the CAS system may include shape recognition software to determine surroundings.

The tracker may be part of a wearable device. The tracker may reveal a position of the wearable device in three-dimensional space given the known and precise relationship between the tracker and the device. For example, the controller may be configured to identify a 3D position of the wearable device (rotation, travel, etc.). Stated differently, the tracker may help provide complete positioning information (e.g., of the wearable device), which may be used by the controller. In an example, the wearable device may define an axis. The controller may be configured to determine a projected position extending along the axis of the wearable device and determine to display a crosshair on the AR system at the projected position. For example, the projected position may be on a surface. It is understood that the crosshair could be replaced with a dot, an arrow, or some other indicator displayed by the AR system.

In an example, the CAS system may comprise a user interface (for example, as may be displayed on the AR display) as will be described. Information displayed on the AR display may mirror a display on a surgical touch screen, such as for planning. Information displayed on the AR display may be a virtual user interface (visible only to the wearer of the AR display). The virtual user interface may have specific parameters that may be adjusted for surgical planning (trajectory, version, inclination, humeral head resection depth, or other similar parameters for various orthopedic surgeries, etc.). A surgeon using the tracked wearable device may interact with the virtual user interface. For example, the position tracking system may interact with the controller to determine where the surgeon is aiming. In some embodiments, the virtual user interface may have one or more virtual buttons. The surgeon may advance the crosshair to a virtual button to make a selection. Selection of a button may require an input. Examples of inputs include one or more of a physical button on the wand configured to send a signal either wired or wirelessly to the controller, a point and hold determination, a finger gesture, a hand gesture, a head gesture, eye gaze, voice, a directional exhale, a foot pedal, or an audible click at a predetermined frequency or frequencies. For example, the audible click may be a result of depressing a metal clicker to create an audible click at a predetermined frequency or frequencies (the controller may be configured to listen for the click, so in some embodiments, audible refers to audible to the controller (advantageously, the click may be audible to the user so that they know the input was made (user feedback)). Stated differently, the audible click may be an acoustic waveform of a predetermined frequency/frequencies and/or amplitude (s). It is understood that combinations of inputs are contemplated as comprising an input, for example, an input may be an eye gaze coupled with a foot pedal press (e.g., within a predetermined time of the eye gaze).

FIG. 4 is a flowchart of a process 100 of the CAS system. The CAS system may comprise an augmented reality (AR) system configured to display augmented reality information including a virtual control element. The virtual control element may be part of a virtual user interface displayed on an AR display. The CAS system may comprise a position tracking system separate from the AR system, wherein the position tracking system is configured to track positions of a physical object (such as described above at FIG. 2 or 3) for interacting with the virtual control element. The CAS system may comprise a controller.

At step 102, the controller may be configured to display augmented reality (AR) information including the virtual control element. An example use case for the virtual user interface may be intra-operative planning, such as for a surgical procedure. The virtual user interface may have specific parameters that may be adjusted for surgical planning (trajectory, version, inclination, resection depth, or other similar parameters for various orthopedic surgeries, etc.). A surgeon using the tracked wearable device may interact with the virtual user interface. The surgeon may navigate the virtual user interface like a menu.

At step 104, the controller may be configured to receive (e.g., detect) a first input indicating that a physical object (for example, the tracked wand (FIG. 2) or tracked wearable (FIG. 3)) is interacting with the virtual control element. For example, the surgeon may advance the physical object so that it is aligned with a virtual button to make a selection. Alignment may be displayed as a crosshair. Selection of a button may require an input. Examples of inputs are described above at FIGS. 2 and 3. Preferably the input is depressing a foot pedal and/or depressing a metal clicker to create an audible click at a predetermined frequency (the controller may be configured to listen for the click). In some embodiments, the input is depressing the foot pedal and depressing the metal clicker (each being detected by the controller).

At step 106, the controller may be configured to determine a change in position of the physical object interacting with the virtual control element indicating a first adjustment. Adjustment may be to a trajectory for example. An adjustment may be based on what happens between two inputs, for example, based on the location (or change of location) of the physical object.

At step 108, the controller may be configured to receive (e.g., detect) a second input. Depending on a portion of the virtual user interface being navigated, the second input may indicate a second adjustment. For example, the second adjustment may be an adjustment to a scalar increment (for example, distance (e.g., mm) or degrees). Example increments include 0.1 mm increments, 0.5 mm increments, 0.1 degree increments, or 0.5 degree increments.

Alternatively, the second input may confirm the first adjustment. Examples of inputs are described above at FIGS. 2 and 3. Preferably the input is depressing a foot pedal and/or depressing a metal clicker to create an audible click at a predetermined frequency (the controller may be configured to listen for the click). In some embodiments, the input is depressing the foot pedal and depressing the metal clicker (each being detected by the controller).

At step 110, the controller may be configured to store one or more of the first adjustment or the second adjustment.

Figure 5A:
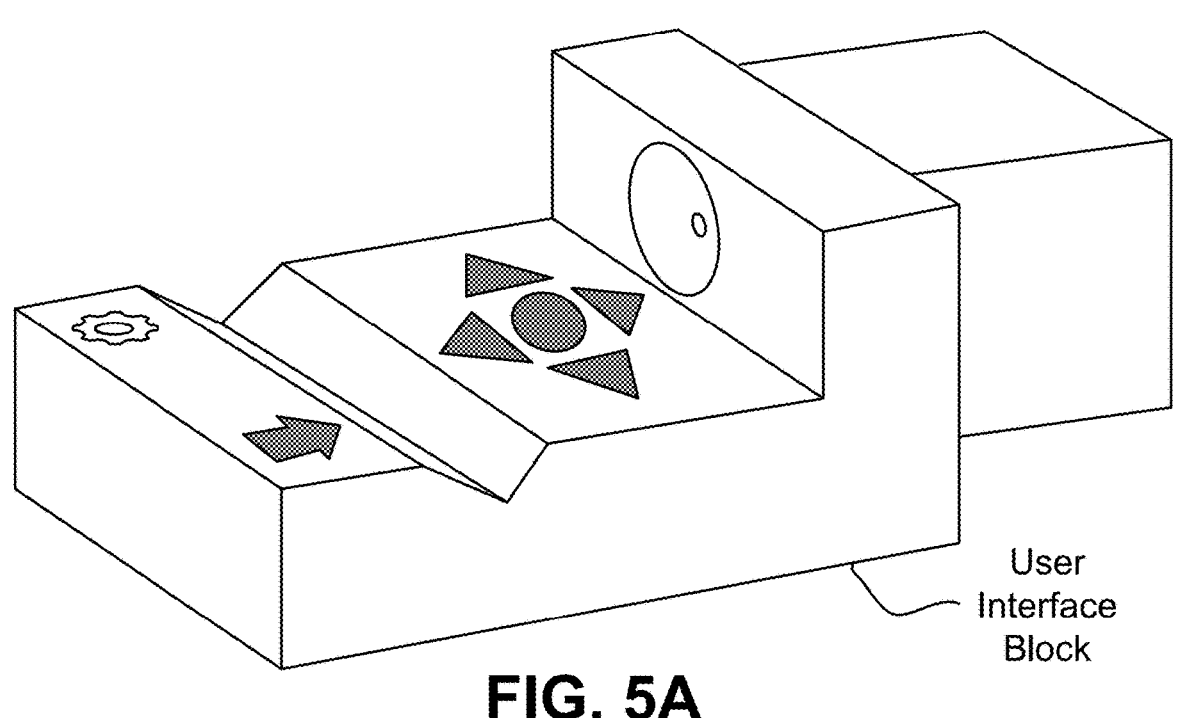
FIG. 5A depicts a registration block for use with an AR display.

FIG. 5A depicts a registration block for use with an AR display (e.g., as a user interface). For example, the block may have engraved, machined, or otherwise permanently indicated markings. Example markings may indicate functions that find use with surgical planning. For example, the markings may represent settings, next screen, left, right, up, down, or enter. The controller may be configured to determine a projected position extending along an axis of a tracked physical object (for example, the tracked wand (FIG. 2) or tracked wearable (FIG. 3)). The controller may be configured to display a crosshair on the AR system at the projected position. For example, the projected position may be on a surface of the block. The position tracking system may exhibit sufficient accuracy to distinguish a position of the projected position among the various markings.

In an example, the CAS system may cause a virtual user interface to be displayed on the AR display. A surgeon using the tracked physical object may interact with the virtual user interface via the block. For example, the position tracking system may interact with the controller to determine where the surgeon is aiming on the block. The surgeon may advance the crosshair to a marking corresponding to a virtual button to make a selection. Stated differently, the virtual user interface may be navigated by selecting an appropriate marking. Selection of a marking may require an input. Examples of inputs are described above at FIGS. 2 and 3.

Figure 5B:
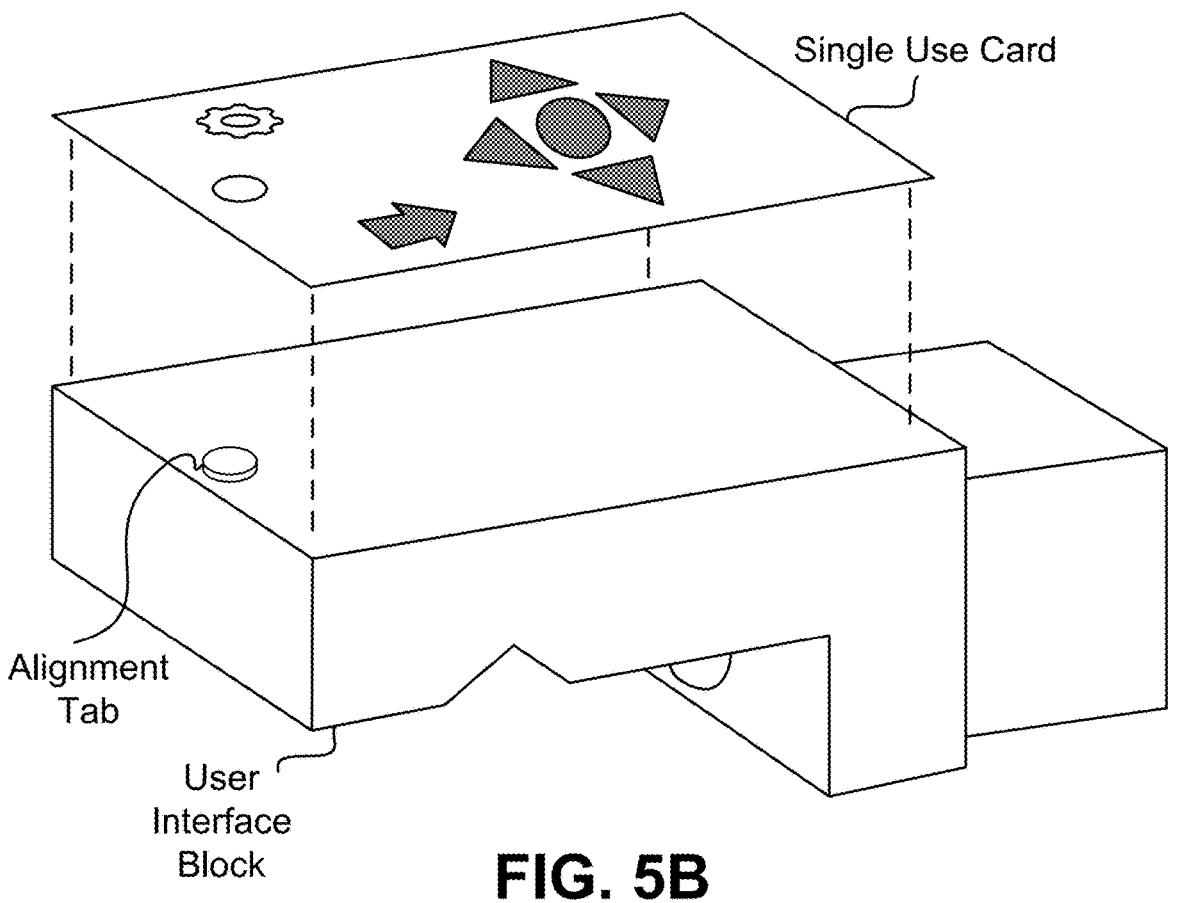
FIG. 5B depicts another embodiment of a registration block for use with an AR display.

FIG. 5B depicts a registration (e.g., user interface) block for receiving a single use card for use with an AR display. For example, the single use card may have markings. The single use card may be part of a set. A single use card may be swapped out for different clinical surgeries or for different portions of a single surgical workflow. A single use card may allow for quickly adapting to new capabilities and new surgical workflows. Information may be incorporated into the single use card, e.g., so the CAS system knows the configuration.

Example markings may indicate functions that find use with surgical planning. For example, the markings may represent settings, next screen, left, right, up, down, or enter. The markings may also indicate planning adjustments to be made by the surgeon. The controller may be configured to determine a projected position extending along an axis of a tracked physical object (for example, the tracked wand (FIG. 2) or tracked wearable (FIG. 3)). The controller may be configured to display a crosshair on the AR system at the projected position. For example, the projected position may be on a surface of the block. The position tracking system may exhibit sufficient accuracy to distinguish a position of the projected position among the various markings.

In an example, the CAS system may cause a virtual user interface to be displayed on the AR display. A surgeon using the tracked physical object may interact with the virtual user interface via the block. For example, the position tracking system may interact with the controller to determine where the surgeon is aiming on the block. The surgeon may advance the crosshair to a marking corresponding to a virtual button to make a selection. Stated differently, the virtual user interface may be navigated by selecting an appropriate marking. Selection of a marking may require an input. Examples of inputs are described above at FIGS. 2 and 3.

Figure 6:
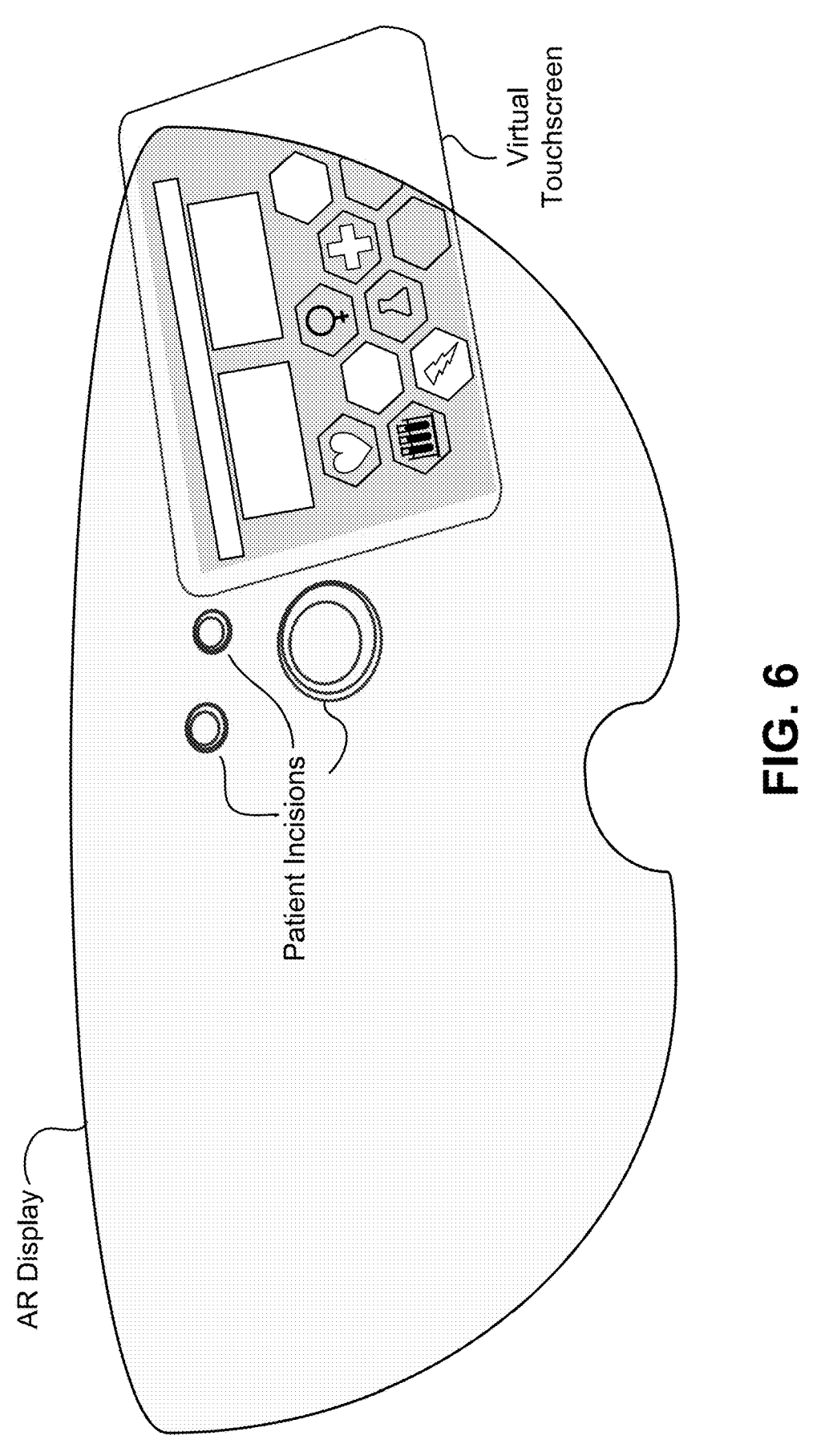
FIG. 6 depicts a schematic of an AR display superimposing a virtual user interface on a surface.

FIG. 6 depicts a schematic of an AR display superimposing a virtual user interface on a surface. Physically, the surface may be a blank surface (such as a white board). However, the CAS system may cause a virtual user interface to be displayed on the AR display (visible only to the wearer of the AR display). The virtual user interface may mirror a display on a surgical touch screen, such as for planning. The virtual user interface may have specific parameters that may be adjusted for surgical planning (trajectory, version, inclination, resection depth, or other similar parameters for various orthopedic surgeries, etc.). The virtual user interface may have selectable modules or virtual buttons. The virtual interface may also enable placement of an external video feed, such as a video call, surgical technique video, etc. The virtual user interface may be best observed when the AR display user looks at the surface.

A surgeon using a tracked physical object (for example, the tracked wand (FIG. 2) or tracked wearable (FIG. 3)) may interact with the virtual user interface. For example, the position tracking system may interact with the controller to determine where the surgeon is aiming. The surgeon may advance the crosshair to a virtual button to make a selection. Selection of a button may require an input. Examples of inputs are described above at FIGS. 2 and 3. In some embodiments, the surface may have some identifying markers such as an exit button or widget buttons to change the users view. For example, the AR display may include pinnable widgets (for example, dashboard widgets may be preset with surgeon preference to flip through screens as appropriate at points in workflow). The virtual user interface may comprise control positions. The virtual user interface may also change with instruments in the surgeon's field of view.

The CAS system may provide an interface for control with an AR display for virtual planning. The virtual control element can be pinned to a location in the surgical theater (placeable by surgeon), such that when the system determines that the location is in the field of view of the AR display, the controller is configured to cause the AR display to display the virtual control element. If the surgeon looks away, the controller is configured to cause the AR display to not display the virtual control element. The system camera (s) can recognize the wand or wearable and assign a vector or point to use as selector. The AR system can include virtually added tool pointer for selecting virtual buttons, for example. The pointer may be used to interact with 3D CT slices by scrolling of a slider bar to change which 2D slice is displayed or moving the pointer up and down along a specific trajectory may scroll through various 2D slices in the 3D CT slice data. Breaking a plane with the wand or wearable at the location of a virtual 3D object (like a cut guide) may allow virtual rotation of the object.

In a first embodiment, a computer aided surgery (CAS) system is provided. The CAS system comprises an augmented reality (AR) system configured to display augmented reality information including a virtual control element; a position tracking system separate from the AR system, wherein the position tracking system is configured to track positions of a physical object for interacting with the virtual control element; a controller configured to: receive planning information for a surgical procedure; determine a first input indicating that the physical object is interacting with the virtual control element; determine a change in position of the physical object interacting with the virtual control element indicating a first adjustment to a parameter of the planning information; receive a second input that either indicates a second adjustment to a parameter of the planning information different from the first adjustment or confirms the first adjustment to the planning information; and store the adjustment to the planning information. In some embodiments, the physical object is attached to a plurality of reflective elements. In some embodiments, the first adjustment to the planning information is a trajectory. In some embodiments, the second adjustment to the planning information is an adjustment to a scalar increment. In some embodiments, the second input confirms the first adjustment.

In some embodiments, the first or second input is a foot pedal depressed by a user. The controller receives a signal based on the press.

In some embodiments, the first or second input is an audio input from a user. In some embodiments, the first or second input is an audible click at a predetermined frequency or frequencies. The controller has a microphone to detect the input.

In some embodiments, the second input is movement by the user, such as a finger gesture, hand gesture, position change, etc., detected by a camera of the controller. The controller may be configured with shape recognition capabilities.

In some embodiments, the controller is further configured to determine a projected position extending along an axis of the physical object and determine to display a crosshair on the AR system at the projected position.

In some embodiments, the parameter of the planning information is displayed on a virtual planning screen as part of the augmented reality information. In some embodiments, the controller is further configured to display the virtual control element as part of a menu displayed when a user of the AR system looks at a specific area in an operating room. In some embodiments, the area is a white board (e.g., a blank surface to akin to a projection screen) placed upon a patient or otherwise accessible in a sterile field. In some embodiments, the area is a registration block adjacent to a patient. In some embodiments, the area is a portion of the user's clothing.

In some embodiments, the controller is further configured to cause the AR system to display a plurality of virtual control elements, wherein each of the virtual control elements has a different planning information function.

In a second embodiment, a method of pre-operative planning is provided. The method comprises displaying augmented reality (AR) information including a virtual control element; detecting a first input indicating that a tracked physical object is aligned with the virtual control element; determining a change in position of the physical object interacting with the virtual control element indicating a first adjustment to a parameter of a surgical planning information; and detecting a second input, wherein the second input is a second adjustment to a parameter of the planning information different from the first adjustment or confirms the first adjustment to the planning information; and storing one or more of the first adjustment or the second adjustment. In some embodiments, the tracked physical object is attached to a plurality of reflective elements. In some embodiments, the first or second input is a foot pedal depressed by a user. In some embodiments, the first or second input is an audio input from a user. In some embodiments, the first or second input is an audible click at a predetermined frequency or frequencies.

The embodiments of the present disclosure described above are intended to be merely examples; numerous variations and modifications within the scope of this disclosure. Accordingly, the disclosure is not to be limited by what has been particularly shown and described. All publications and references cited herein are expressly incorporated by reference in their entirety, except for any definitions, subject matter disclaimers or disavowals, and except to the extent that the incorporated material is inconsistent with the express disclosure herein, in which case the language in this disclosure controls.

The invention claimed is:

1. A computer aided surgery (CAS) system, comprising:
an augmented reality (AR) system configured to display augmented reality information including a virtual control element to a user wearing a head mounted display;
a position tracking system separate from the AR system, wherein the position tracking system is configured to track positions of a physical object attached to a plurality of reflective elements, the positions of the physical object for interacting with the virtual control element;
a controller configured to:
determine an axis of the physical object based on the position of the physical object;
receive planning information for a surgical procedure;
determine a first input indicating that the physical object is interacting with the virtual control element at a projected position extending along the axis of the physical object;
determine a change in position of the axis of the physical object interacting with the virtual control element indicating a first adjustment to a parameter of the planning information;
receive a second input that either indicates a second adjustment to a parameter of the planning information different from the first adjustment or confirms the first adjustment to the planning information; and
store the adjustment to the planning information.

2. The system of claim 1, wherein the first adjustment to the planning information is a trajectory.

3. The system of claim 2, wherein the second adjustment to the planning information is an adjustment to a scalar increment.

4. The system of claim 1, wherein the first or second input is a foot pedal depressed by a user.

5. The system of claim 1, wherein the first or second input is an audio input from a user.

6. The system of claim 1, wherein the first or second input is an audible click.

7. The system of claim 1, wherein the second input is movement by the user.

8. The system of claim 1, wherein the controller is further configured to display a crosshair on the AR system at the projected position extending along the axis of the physical object.

9. The system of claim 1, wherein the parameter of the planning information is displayed on a virtual planning screen as part of the augmented reality information.

10. The system of claim 1, wherein the controller is further configured to display the virtual control element as part of a menu displayed when a user of the AR system looks at a specific area in an operating room.

11. The system of claim 10, wherein the area is a white board placed upon a patient or otherwise accessible in a sterile field.

12. The system of claim 10, wherein the area is a registration block adjacent to a patient.

13. The system of claim 10, wherein the area is a portion of the user's clothing.

14. The system of claim 1, wherein the controller is further configured to cause the AR system to display a plurality of virtual control elements, wherein each of the virtual control elements has a different planning information function.

15. A method comprising:

displaying augmented reality (AR) information including a virtual control element to a user wearing a head mounted display;

detecting a first input indicating that a tracked physical object is aligned with the virtual control element, wherein the tracked physical object is attached to a plurality of reflective elements, the plurality of reflective elements detectable by position tracking system separate from the AR system, wherein the position tracking system is configured to track positions of the physical object for interacting with the virtual control element at a projected position extending along the axis of the physical object;

determining an axis of the physical object based on the position of the physical object;

determining a change in position of the axis of the physical object interacting with the virtual control element indicating a first adjustment to a parameter of planning information for a surgical procedure; and detecting a second input, wherein the second input is a second adjustment to a parameter of the planning information different from the first adjustment or confirms the first adjustment to the planning information; and storing one or more of the first adjustment or the second adjustment to the planning information.

16. The method of claim 15, wherein the first or second input is a foot pedal depressed by a user.

17. The method of claim 15, wherein the first or second input is an audio input from a user.

18. The method of claim 15, wherein the first or second input is an audible click.

19. The method of claim 15, further comprising displaying a crosshair on the head mounted display at the projected position extending along the axis of the physical object.

20. The method of claim 15, further comprising displaying a plurality of virtual control elements, wherein each of the virtual control elements has a different planning information function.

* * * * *